United States Patent [19]

Lees

[11] Patent Number: 4,647,445

[45] Date of Patent: Mar. 3, 1987

[54] RADIOLABELLED LIPOPROTEINS AND METHOD FOR MAKING SAME

[75] Inventor: Robert S. Lees, Brookline, Mass.

[73] Assignee: Massachusetts Institute of Technology, Cambridge, Mass.

[21] Appl. No.: 594,244

[22] Filed: Mar. 28, 1984

[51] Int. Cl.$^4$ .................... A61K 43/00; A61K 49/00; A61K 37/00

[52] U.S. Cl. ........................................ 424/1.1; 424/9; 514/2

[58] Field of Search ................. 424/1.1, 9, 177; 514/2

[56] References Cited

U.S. PATENT DOCUMENTS

| | | | |
|---|---|---|---|
| 4,057,617 | 11/1977 | Abramouici et al. | 424/1.1 |
| 4,293,537 | 10/1981 | Wong | 424/1.1 |
| 4,364,920 | 12/1982 | Winchell | 424/1.1 |
| 4,424,200 | 1/1984 | Crockford et al. | 424/1.1 |
| 4,472,509 | 9/1984 | Gansow et al. | 424/1.1 |

OTHER PUBLICATIONS

Roberts et al, Abstracts from the 53rd Scientific Sessions, American Heart Association, Nov. 17–20, 1980, Miami Beach, Fla.

Gary E. Krejarek and Karen L. Tucker, "Covalent Attachment of Chelating Groups to Macromolecules", *Biochemical and Biophysical* Research Communications, vol. 77, No. 2, 1977, pp. 581–585.

Alan G. Jones, Chris Orvig, Harvey S. Trop, Alan Davison, and Michael A. Davis, "A Survey of Reducing Agents for the Synthesis of Tetraphenylarsonium Oxotechnetiumbis(ethanedithiolate) from [$^{99}$Tc]Pertechnetate in Aqueous Solution", J. Nuclear Medicine, vol. 21, No. 3, pp. 279–281, 1980.

D. J. Hnatowich, W. W. Layne, and R. L. Childs, "The Preparation and Labeling of DTPA-Coupled Albumin, *Int'l Journal of Applied Radiation and Isotopes*, 33 327–332, 1982.

Bruno V. DePamphilis, Alan G. Jones, Alan Davison, "Ligand-Exchange Reactivity Patterns of Oxotechnetium (V) Complexes," *Inorganic Chemistry* 22: 2292–2297, 1983.

D. J. Hnatowich, W. W. Layne, R. L. Childs, D. Lanteigne, M. A. Davis, T. W. Griffin, P. W. Doherty, "Radioactive Labeling of Antibody: A Simple and Efficient Method", *Science* 220: 613–615, 1983.

Joseph Steigman, Hazel P. Williams, and Nathan A. Solomon, "The Importance of the Protein Sulfhydril Group in HSA Labeling with Technetium 99m" Proceedings of 22 Annual Meeting, *Journal of Nuclear Medicine* 16: 573, 1975 (Abst.).

Robert H. Rice and Gary E. Means, "Radioactive Labeling of Proteins in vitro", *Journal of Biological Chemistry* 246:3, pp. 831–832, 1971.

J. K. Murphy, T. C. Monchesky, G. Steiner, "In vitro Labelling of β-Apolipoprotein with $^3$H or $^{14}$C and Preliminary Application to Turnover Studies," *Journal of Lipid Research* 16: 1–6, 1975.

he 56th Scientific Sessions Oct. 1983.

B. A. Khaw, H. K. Gold, M. Goldman, J. T. Fallon, T. Brady, T. Yasuda, B. Rosen, I. Pykett, H. W. Strauss, E. Haber, "Iomographic NMR Imaging of Experimental Myocardiol Infactum Using Paramagnetic Manganese Labeled Anti-Myosin Fab. *Abstracts of the 56th Scientific Sessions* Oct. 1983.

Robert J. Lusby, MD., FRCS, FRACS, D. Linda D. Ferrell, MD., Barry L. Englestad, MD., David C. Price, D. M., FRCP(C), Martin J. Lipton, MD., and Ronald J. Stoney, MD., "Vessel Wall and Indium–III–-Labelled Platelet Response to Carotid Endarterectomy," *Surgery* Mar. 1983, vol. 93, No. 3, pp. 424–432.

*Primary Examiner*—Christine M. Nucker
*Attorney, Agent, or Firm*—Cesari and McKenna

[57] ABSTRACT

Lipoproteins radiolabelled with an isotope of technetium substantially retain their native structure and biological function. The lipoproteins can be radiolabelled by simultaneous reduction of pertechnetate and lipoprotein with sodium dithionite at pH 8-9. The resulting radiolabelled lipoproteins can be used as probes for extracorporeal imaging to analyze lipoprotein metabolism.

11 Claims, 2 Drawing Figures

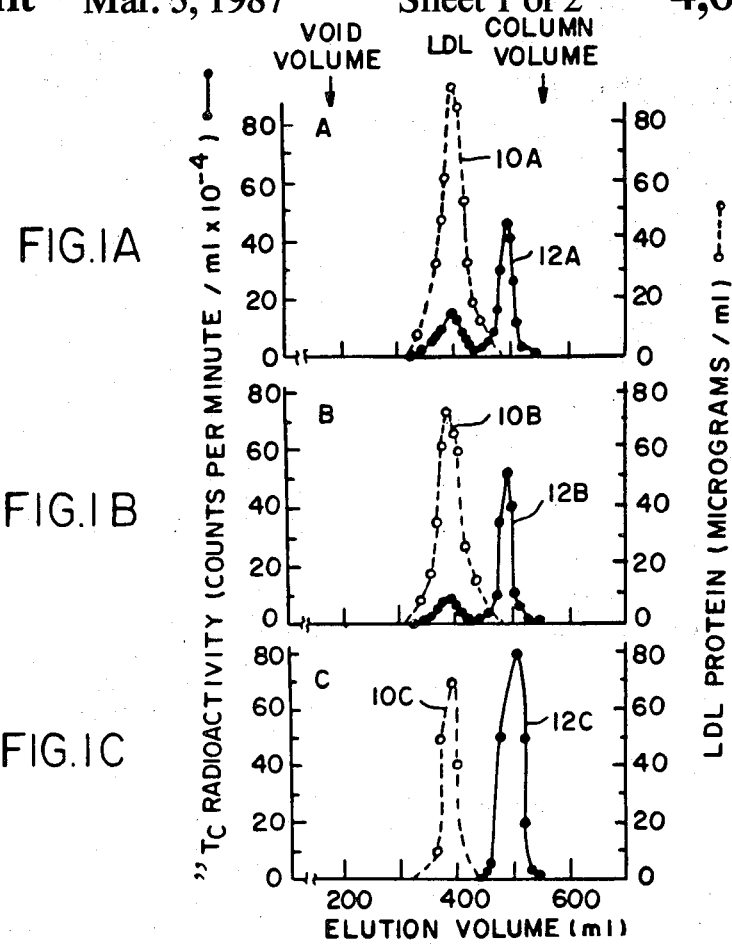
FIG.1A
FIG.1B
FIG.1C
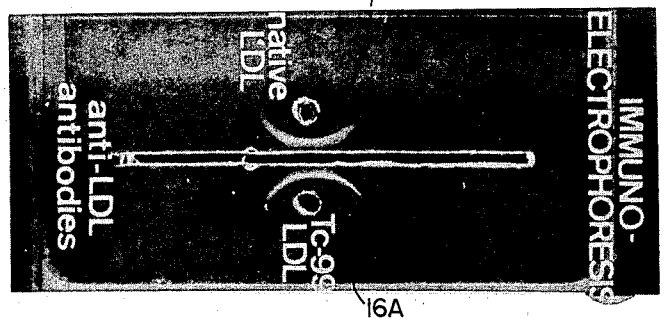
FIG.2A
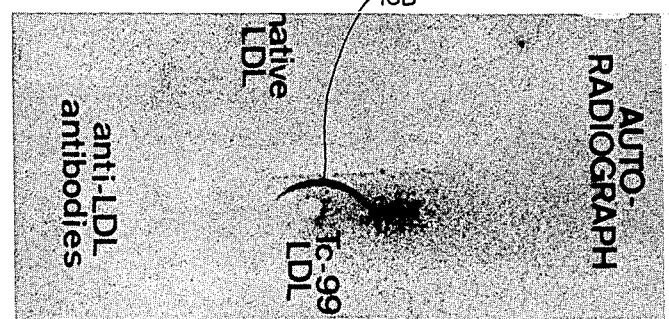
FIG.2B

TABLE 1

BIODISTRIBUTION OF $^{99m}$TC-LDL IN THE RABBIT

| ORGAN | | PERCENT OF INJECTED RADIOACTIVITY PER GRAM (MEAN ± S.E.M.) | PERCENT OF INJECTED RADIOACTIVITY PER ORGAN (MEAN ± S.E.M.) |
|---|---|---|---|
| VENOUS BLOOD | | 0.03 ± 0.01 | --- |
| LIVER | | 0.19 ± 0.02 | 21.1 ± 1.3 |
| SPLEEN | | 0.22 ± 0.04 | 0.4 ± 0.1 |
| ADRENAL | (WHOLE)* | 0.81 ± 0.19 | 0.2 ± 0.1 |
| | (CORTEX)* | 0.92 ± 0.09 | 0.3 ± 0.1 |
| | (MEDULLA)* | 0.59 ± 0.06 | 0.1 ± 0.1 |
| KIDNEY | (CORTEX) | 0.11 ± 0.02 | 2.9 ± 0.4 |
| | (MEDULLA) | 0.04 ± 0.01 | 0.9 ± 0.2 |
| SMALL BOWEL | | 0.01 ± 0.00 | 1.3 ± 0.2** |
| LARGE BOWEL | | 0.05 ± 0.01 | 2.3 ± 0.3** |
| MUSCLE | | 0.002 ± 0.0 | 1.6 ± 0.3** |
| AORTA (THORACIC) | | 0.02 ± 0.00 | --- |

*THE ENTIRE ADRENAL GLAND WAS WEIGHED AND COUNTED IN 12 ANIMALS, WHILE CORTEX AND MEDULLA WERE DISSECTED OUT, WEIGHED, AND COUNTED SEPARATELY IN 4 ANIMALS.

**PERCENT OF THE INJECTED DOSE IS EXPRESSED PER 100 GM FOR SMALL AND LARGE BOWEL, WHILE THAT FOR MUSCLE IS EXPRESSED FOR BODY MUSCLE MASS, ASSUMED TO BE 45% OF BODY WEIGHT.

RADIOLABELLED LIPOPROTEINS AND METHOD FOR MAKING SAME

FIELD OF THE INVENTION

The present invention relates to biologically active lipoproteins labelled with radioisotopes especially suited for extracorporeal imaging, and more specifically to lipoproteins labelled with technetium isotopes and methods for making same.

BACKGROUND OF THE INVENTION

In the past, lipoprotein metabolism has been monitored in vivo by introducing intravenously lipoproteins labelled with the radioisotope $^{125}I$, and following the radioactivity with time in blood and/or urine. Since the isotope is a gamma emitter, the radiation image depicts the sites of metabolic activity and to some extent the degree thereof. Lipoprotein metabolism is of special interest because of its close association with atherosclerosis. For example, as set forth in U.S. Application serial number 425,187, filed Sept. 18, 1982, atherosclerotic lesions take up $^{125}I$-labelled low density lipoproteins, and these lesions can be monitored by extracorporeal gamma radiation imaging in animals and man after introduction of the lipoproteins in the bloodstream. However, these measurements are somewhat limited by the poor imaging characteristics of $^{125}I$.

Isotopes, such as Technetium-99m, are often used in nuclear medicine because their short half life and high-energy gamma emmission provide for excellent external imaging while permitting in vivo absorption of only a low dose of radioactivity. However, coupling these isotopes to lipoproteins (and to biological molecules in general) may result in loss of native structure or biological function of the coupled molecules. Lipoproteins are especially unstable in that they readily denature at pH 7 and below. This restricts the range of chemical procedures that can be used to couple radioisotopes to lipoproteins. Furthermore, biological molecules also have "active sites" (parts of their molecules that are responsible for their biological interactions with other body chemicals or structural components), and attachment of a radioisotope to these sites may interfere chemically or sterically with these interactions. Therefore, even when an isotope-coupled molecule is not denatured, it is not necessarily biologically active in the same way and to the same degree as its non-coupled counterparts. Such an isotope-coupled molecule would not suffice for studying a particular biological reaction of interest.

Technetium-99m($^{99m}Tc$), is an isotope especially suited for external imaging. For study of technetium chemistry, the more stable isotope, 99Tc, is often used for convenience. This was demonstrated by Jones et al (Journal of Nuclear Medicine 21:279-281, 1980) and DePamphilis et al (Inorganic Chemistry 22:2292-2297, 1983) to form stable technetium-dithiolate chelates by reduction of pertechnetate ($TcO_4^-$). A reducing agent effective in making this stable complex is sodium dithionite. While the yield was not maximal at pH 11 or higher, some stable technetium-dithiolate chelates were formed at physiologic pHs (pH 5-8). There was no suggestion in those studies that technetium would form a stable complex with proteins and lipoproteins.

An abstract published by Steigman (Journal of Nuclear Medicine 16:573, 1975) discloses a technetium-horse serum albumin (HSA) complex prepared by reduction of pertechnetate with ascorbic acid and ferric chloride, and subsequent attachment to HSA through a series of steps in pH environments ranging from 9 to 2. These low pHs would denature lipoproteins. Accordingly, Steigman's procedure for complexing technetium to albumin could not be applied to radiolabel lipoproteins.

Many radioisotopes that have good imaging characteristics are known to chelate diethylene triamine pentaacetic acid (DTPA), a bifunctional chelating agent which can be covalently bound to amine groups of proteins. DTPA has been coupled to albumin (Krejarek and Tucker, Biochemical and Biophysical Research Communications 77:581-585, 1977; Hnatowitch et al, International Journal of Applied Radiation and Isotopes 33:327-332, 1982), and to immunoglogulin G (IgG) (Hnatowitch et al, Science 220:613-615, 1983), and the coupled product has been chelated with indium. DTPA is known to chelate other metals such as Tc, Pb, Hg, Ga, and Mn.

Krejarek and Tucker couple DTPA to HSA utilizing a carboxycarbonic anhydride of DTPA. The coupling procedure involves an initial reaction at pH 7-8, then dialysis against acetate buffer at pH 5.5, and subsequent isolation of the DTPA-HSA product by column chromatography at pH 3.5. Indium is added at pH 3.5 to chelate DTPA-HSA. The pHs employed by Krejarek and Tucker would also denature lipoproteins.

Hnatowitch uses a cyclic anhydride of DTPA, which appears to be more reactive with some proteins than the carboxycarbonic anhydride of DTPA, and therefore can be coupled to these proteins with greater efficiency and under milder reaction conditions. Optimal coupling occurs at pH 7 (again, a pH which may not be useable with lipoproteins).

Thus, both DTPA coupling procedures described above by Krejarek and Hnatowitch are not directly applicable to lipoproteins for subsequent chelation with a radioisotope. Even slight changes in reaction conditions are known to affect the resulting product. For example, altering reaction conditions can lower the efficiency of DTPA coupling to protein, which reduces the amount of radiolabel that can be chelated to the DTPA-coupled protein. The resulting product may have insufficient specific radioactivity for practical use. Also, as with attachment of any isotope to a biological molecule, the resulting product may not have the desired biological activity. Such changes in biological activity are even more likely to occur when larger compounds, such as DTPA, are coupled to the biomolecule.

SUMMARY OF THE INVENTION

Accordingly, the present invention aims to provide an improved radiolabelled lipoprotein, that is suitable for extracorporeal imaging.

It is a further object of the present invention to provide an improved radiolabelled lipoprotein that substantially retains its native biological activity and can be used to monitor lipoprotein metabolism in vivo.

Yet another object of the present invention is to provide an improved radiolabelled lipoprotein that is relatively inexpensive and easy to prepare.

Yet another object of the present invention is to provide a method for radiolabelling a lipoprotein or other molecule having biological activity exhibited by a lipoprotein with isotopes suitable for extracorporeal imaging.

Other objects will in part be obvious, and will, in part, appear hereinafter.

Briefly, the invention comprises biologically active lipoproteins, or other molecules having one or more of the biological functions of lipoproteins, which are radiolabelled with technetium (Tc). More specifically, the invention comprises biologically active low density lipoproteins (LDL) radiolabelled with a technetium isotope, and methods for making such labelled lipoproteins.

A preferred method for preparing technetium-labelled low density lipoprotein complexes (Tc-LDL) is by simultaneous reduction of LDL and pertechnetate (TcO$_4^-$) with sodium dithionite at pH 8-9. LDL and TcO$_4^-$ are mixed together, freshly dissolved sodium dithionite is added, and the mixture is stirred for thirty minutes at room temperature. The mixture is maintained at pH 8-9 throughout the coupling procedure. Tc-LDL is separated from unreacted technetium and dithionite by either molecular sieve chromatography, or by filtration.

Alternatively, the chelating agent, DTPA, may be coupled to LDL, and the coupled DTPA-LDL product is then isolated. A technetium isotope is subsequently chelated to the DTPA-LDL by reduction in the presence of sodium dithionite, and the radiolabelled Tc-DTPA-LDL complex is separated from uncomplexed technetium by molecular sieve chromatography.

BRIEF DESCRIPTION OF THE FIGURES

FIG. 1A represents a chromatography column elution profile from a reaction mixture of LDL, TcO$_4^-$, and sodium dithionite, incubated according to the methods. Solid lines represent radioactivity and dotted lines protein.

FIG. 1B represents a chromatography column elution profile from a reaction mixture of DTPA-LDL, TcO$_4^-$, and sodium dithionite, incubated according to the methods. Solid lines represent radioactivity and dotted lines protein.

FIG. 1C represents a chromatography column elution profile from mixtures of native LDL and TcO$_4^-$, incubated according to the methods but with no sodium dithionite. Solid lines represent radioactivity and dotted lines protein.

FIG. 2A represents immunoelectrophoresis profiles of native LDL and Tc-LDL.

FIG. 2B represents a subsequent autoradiograph of the immunoelectrophoresis profile of Tc-LDL.

TABLE 1 represents the biodistribution of $^{99m}$Tc-LDL in the rabbit 18 hr after intravenous injection of 4-8 mCi of human $^{99m}$Tc-LDL.

DETAILED DESCRIPTION OF THE PREFERRED EMBODIMENTS

Preparation of Low Density Lipoproteins

Low density lipoproteins are isolated from normal human plasma, e.g. by sequential flotation using equilibrium density centrifugation (Hatch and Lees, Advances in Lipid Research 6:1-68, 1968). The density of plasma is adjusted to 1.025 g/ml by addition of a potassium bromide solution, and ultracentrifuged for 22 hrs at 100,000 g. The supernatant (containing lipoproteins having a density less than 1.025 g/ml) is removed and discarded. The density of the infranatant is then adjusted to 1.050 g/ml by another addition of the potassium bromide solution and is ultracentrifuged for a second 22 hrs at 100,000 g. The second supernatant (containing low-density lipoproteins having a density between 1.025 to 1.050 g/ml) is removed and dialyzed for 24 hrs against a sodium bicarbonate buffer containing 0.15 M NaCl and 1.0 mM disodium EDTA, pH 8.6, or alternatively used without dialysis. The LDL is filtered through a 0.22 micron filter before use to remove any bacterial contamination.

Other procedures may also be used to purify LDL. These include heparin-manganese chloride precipitation (Fredrickson et al, New England Journal of Medicine 276:32-44,94-103,148-156,215-226,273-281, 1967) or heparin-agarose affinity chromatography (Fielding and Fielding, Proceedings of National Academy of Science USA 77:3327-3370, 1980) followed by ultracentrifugation in a discontinuous density gradient (Hatch and Lees, Advances in Lipid Research 6:1-68, 1968).

Radiolabelling Procedures

LDL can be labelled directly with technetium (Tc), or indirectly through covalent attachment of a strong chelating group such as diethylenetriamine pentaacetic acid (DTPA), which is known to chelate a variety of metals including radioisotopes such as indium-111.

1. Direct Labelling of LDL with Techcetium

Technetium is directly coupled to lipoproteins by the following procedure. 50 mCi $^{99m}$Tc (in the form of TcO$_4^-$) in a 0.5 ml aqueous solution, is added to 2-6 mg LDL in 0.5 ml of a 0.2 M sodium bicarbonate, pH 8, and mixed thoroughly for 10 minutes at room temperature. The pH is raised to 8-9 if necessary with 0.25 M sodium hydroxide, and the mixture is reduced by the addition of 10 mg sodium dithionite (57.5 umoles) freshly dissolved in 0.5 ml distilled water. The mixture is gently stirred for 30 minutes at room temperature.

The radiolabelled LDL fraction is separated from denatured or aggregated LDL, uncoupled technetium, and sodium dithionite by molecular sieve chromatography. A 2×5 cm column of Sephadex G50M, equilibrated with a bicarbonate-EDTA buffer [containing 0.2 M sodium bicarbonate, pH 8, and 0.001 M disodium ethylene diamine tetraacetic acid (EDTA)], is suitable for separation. The column is standardized with blue dextran and potassium iodide to determine the void volume and the column volume, respectively. The reaction mixture is applied to the column and bicarbonate-EDTA buffer is used to elute column fractions. The macromolecular radioactive peak that elutes at a position characteristic for LDL is isolated and is ready for use.

2. Indirect Coupling of Technetium to Lipoproteins

DTPA is coupled to lipoproteins by the following method as described by Krejarek and Tucker. An aliquot of 5.5-25 ul (0.7 to 3.2 umoles) of a solution of a carboxycarbonic anhydride of DTPA is added to 2-3 ml of LDL (6 mg, 1.2×10$^{-2}$ umoles) and the mixture is gently agitated. The anhydride to protein molar ratio is as high as 300. During the reaction, the pH is maintained at 8 with 0.2 M NaHCO$_3$. The mixture is stirred for 15 minutes at room temperature and incubated at 4° C. for 18 hrs. Unreacted DTPA is removed by dialysis against the bicarbonate-EDTA buffer.

Alternatively, the cyclic anhydride of DTPA is prepared by the method of Hnatowich et al, and is used to couple DTPA to lipoproteins by the following procedure.

Ten ug cyclic anhydride of DTPA is added to 3 mg of LDL in 1.0 ml 0.05 M sodium bicarbonate buffer at room temperature and the mixture is stirred for 10 minutes. DTPA-coupled lipoprotein is separated from unreacted DTPA by passage over a Sephadex G25 chromatography column equilibrated with 0.2 M sodium bicarbonate buffer pH 8.

Technetium is then chelated to the DTPA-LDL by the procedure described above for direct labelling of native LDL. Technetium, in the form of $TcO_4^-$, is added to the DTPA-LDL, and the mixture is reduced with sodium dithionite at pH 8-9. Technetium-labelled DTPA-LDL is separated from uncomplexed technetium and sodium dithionite by column chromatography.

In some cases, to facilitate handling and experimentation, a technetium isotope with a long half life ($^{99}Tc$), was used instead of $^{99m}Tc$, which has a short half life. For example, the $^{99}Tc$ isotope was used in experiments determining labelling conditions and comparing the physical and chemical properties of the radiolabelled LDL with native LDL, as well as in preliminary in vivo tests demonstrating the biological activity of radiolabelled-LDL. When the $^{99}Tc$ isotope was coupled to LDL, the foregoing labelling methods were followed, except that one uCi $^{99}Tc$ was substituted for 50 mCi $^{99m}Tc$.

Demonstration of Tc-LDL and Tc-DTPA-LDL Coupling

Reaction mixtures from both the direct and indirect radiolabelling methods were analyzed by molecular sieve chromatography to determine whether the foregoing procedures do in fact radiolabel the lipoproteins. Native LDL, heat-denatured LDL, and unreacted technetium were passed through a molecular sieve chromatography column to calibrate the column. Column fractions were monitored for protein and for radioactivity, respectively. Heat-denatured LDL eluted in the void volume. Native LDL eluted at a volume characteristic for its molecular size, and unreacted technetium eluted in the column volume or small molecule peak.

In separate experiments, $^{99}Tc$ was coupled to LDL and DTPA-LDL by reduction with sodium dithionite, in accordance with the methods described above. The resulting mixtures were analyzed by means of the calibrated chromatography column. FIG. 1A depicts resulting elution profiles for the direct-labelling method, i.e. for production of Tc-LDL. The profile 10A represents radioactivity measurements of column eluate, and the profile 12A represents protein assays of the eluate as determined by ultraviolet absorbance at 280 nanometers. The profile 10A indicates that one third to one half of the radioactivity eluted in a macromolecular peak corresponding in position to native LDL. The remaining radioactivity eluted in a volume characteristic of small molecules. As shown by the profiles 10A and 12A, no radioactivity or protein was observed in the void volume.

FIG. 1B depicts the elution profile for the indirect labelling method, i.e. for production of Tc-DTPA-LDL. The profiles 10B and 12B, which correspond with the profiles 10A and 12A, respectively, indicate essentially the same observations for Tc-DTPA-LDL as were recorded for Tc-LDL.

As a control for these experiments, $^{99}TcO_4^-$ and LDL were mixed in accordance with the methods except that no reducing agent was added. FIG. 1C depicts the resulting elution profiles for this mixture. The profiles 10C and 12C, which represent radioactivity measurements and protein assays, respectively, indicate that no radioactivity was detected in the native LDL peak.

Accordingly these chromatographic studies show that technetium does not merely associate with LDL but that when the above coupling methods are used, technetium-lipoprotein complexes are formed either by direct attachment to native LDL, or by indirect chelation with DTPA-LDL. Furthermore, under reaction conditions which do not denature LDL, the use of the ligand DTA does not produce enhanced technetium binding relative to that obtained with native LDL.

In human studies, the technetium-lipoprotein coupling methods described above for radiolabelling lipoproteins must be performed under sterile conditions, which is difficult when column chromatographic procedures are used to isolate the coupled LDL. However, Tc-LDL prepared by dithionite reduction at pH 9 (FIG. 1A) demonstrates no formation of aggregated LDL, as indicated by the absence of radioactivity and protein in the column void volume. The only large molecular weight species formed in the labelling reaction is the radiolabelled LDL. Accordingly, isolation of radiolabelled LDL requires only separation of the large molecular weight LDL from the small molecules, reduced technetium and dithionite, of the reaction mixture. Therefore, radiolabelled LDL may be separated from the reaction components by filtration and washing, a procedure in which sterility is easier to maintain.

For example, Tc-LDL and its reaction mixture were passed through a pre-sterilized 2×5 cm gel-filtration column of Sephadex G50M, as described above.

Effects of pH on the Coupling of Tc to LDL and to DTPA-LDL

The effects of the pH environment on coupling of technetium to LDL and DTPA-LDL were also evaluated by molecular sieve chromatography. Reduction of technetium at pH 10-11 gave labelling efficiencies that ranged from 45% to 70%. However, coupling at these pHs reduced the yield of labelled LDL because it promoted denaturation of native LDL and formation of LDL aggregates which eluted in the void volume upon chromatography. When the process was performed in a pH 8-9 environment, a lower coupling efficiency of 40% resulted. However, the elution profile was similar to that of native LDL, indicating negligible denaturation and aggregation. Accordingly, a pH of 8-9 is preferred for producing technetium-labelled lipoproteins because it provides a relatively high labelling efficiency with minimal physical change in the LDL.

Reducing technetium under mildly alkaline pHs has been reported by Jones et al (referenced above) to produce colloidal $TcO_2$ by a reaction which competes with binding of technetium to lipoproteins, which implies that the labelling methods described herein would not be satisfactory. However, colloidal technetium was not detected in the reaction products obtained from our methods, as indicated by the absence of non-protein-bound high molecular weight radioactive species in the chromatographic void volumes, and at the bottom of the tube on ultracentrifugation. (See FIGS. 1A and 1B and below.)

Physical/Chemical Comparison of Tc-LDL and Tc-DTPA-LDL with Native LDL and Stability of the Tc-LDL Bond The following tests were performed to ascertain the stability of the technetium-LDL bond obtained with my labelling methods, and to compare the physical and chemical properties of the radiolabelled products with native LDL. A strong technetium-lipoprotein bond and retention of the native physical and chemical properties are necessary to ensure that during in vivo use, gamma detection will provide an accurate representation of native lipoprotein activity.

1. The stability of the bonding of technetium to LDL, both directly and by means of DTPA, was investigated by equilibrium density ultracentrifugation. At the appropriate density, LDL floats in the ultracentrifuge, and technetium that was tightly bound to LDL will remain bound and will thus be be found in the supernatant. Technetium that was loosely bound will be separated from LDL and will thus be distributed throughout the tube after ultracentrifugation, while colloidal technetium dioxide would sediment to the bottom of the tube. About 1.5 mg $^{99}$Tc-LDL obtained from the macromolecular chromatographic peaks and having a radioactivity of about 0.1 uCi was ultracentrifuged at a density of 1.063 g/ml for 22 hrs at 100,000 g. The supernatant contained eighty-four percent of the total radioactivity (average of multiple samples). When experiments were repeated with $^{99}$Tc-DTPA-LDL, the supernatant contained seventy-nine percent of the total radioactivity after ultracentrifugation. No concentration of radioactivity was observed at the bottom of the tube.

Controls for the foregoing were also analyzed by ultracentrifugation. When a mixture of pertechnetate and native LDL, incubated without sodium dithionite, was ultracentrifuged, the supernatant contained only five percent of the total radioactivity. Similarly, when reduced technetium (technetium and sodium dithionite incubated without LDL) was ultracentrifuged, the radioactivity did not float in the supernatant.

Accordingly, these results show that most of the radioactivity found in the technetium-labelled lipoproteins is tightly bound to the lipoprotein.

2. Both the stability of the technetium-lipoprotein bond and the physical/chemical properties of the technetium-labelled lipoproteins were analyzed by paper electrophoresis. Various technetium labelled LDL samples (identified below) and controls were electrophoresed in parallel and the strips were stained for lipid and scanned for radioactivity. Electrophoresis of native LDL, $^{99}$Tc-LDL, DTPA-LDL, and $^{99}$Tc-DTPA-LDL, demonstrated single bands with identical LDL mobility. When the electrophoretic strips containing $^{99}$Tc-LDL and $^{99}$Tc-DTPA-LDL were scanned for radioactivity in a strip counter, a single peak of radioactivity was obtained, and these peaks were located in the lipid-stained bands for these materials. A heat-denatured LDL control which was detected by staining, remained at the origin. A control of reduced technetium also remained at the origin as indicated by a single sharp peak of radioactivity. These results show that the radioactivity detected in the lipid-stained bands with LDL mobility represented technetium bound to LDL, either directly or indirectly by means of DTPA, and that the electrophoretic properties of Tc-LDL and Tc-DTPA-LDL were not altered during the radiolabelling procedures or by the low molar ratio of DTPA bound to the protein.

3. The physical/chemical properties of Tc-LDL were further investigated by immunoelectrophoresis and autoradiography, as seen in FIG. 2A and 2B, respectively. In FIG. 2A, precipitin arcs 14A and 16A represent immunoelectrophoresis profiles of native LDL and Tc-LDL, respectively, after exposure to rabbit anti-LDL antiserum. The location and shape of precipitin arc 16A for TC-LDL corresponds to that of arc 14A for native LDL.

FIG. 2B represents an autoradiograph of the same immunoelectrophoresis slide shown in FIG. 2A. The profile 16B represents the distribution of radioactivity present in Tc-LDL after immunoelectrophoresis. Profile 16B shows a single arc, of uniform radioactivity, superimposing the immunoprecipitin arc 16A. The immunoelectrophoresis and autoradiography results further indicate the similarity between Tc-LDL and native LDL with respect to mobility, homogeneity and immunologic identity.

4. The stability of the technetium-LDL bond and the distribution of the label between protein and lipid were investigated by extraction with chloroform-methanol. Upon extraction, the lipid component of LDL solubilizes in the chloroform phase and the protein component of LDL remains in the aqueous phase. Technetium that is loosely bound to LDL is also soluble in the aqueous phase. Radiolabel bound to the protein can be separated from unbound radiolabel by precipitating the protein from the aqueous phase by addition of trichloroacetic acid.

$^{99}$Tc-LDL prepared by the method described above was mixed with chloroform-methanol 2:1 (v/v). After vortexing and centrifugation, the chloroform layer was removed and the radioactivity was measured. Protein from the remaining aqueous layer was precipitated with trichloroacetic acid and the radioactivity in the precipitate was determined. The protein precipitate contained 78–90% of the total radioactivity, while chloroform-extracted lipids contained only 2.4–4.4% of the radioactivity. These results provide further evidence that technetium is strongly bound to LDL. They also indicate that it is bound to the protein component of LDL.

In Vivo Distribution and Behavior of Tc-LDL in Rabbits

In combination, the above results indicate the technetium-labelled lipoproteins exhibit minimal physical and chemical alteration, as shown by similarities between labelled-LDL and native LDL upon electrophoresis, immunoelectrophoresis, and ultracentrifugation. Accordingly, these radiolabelled lipoproteins are likely to provide an accurate representation of lipoprotein metabolism in vivo. The following tests were performed to investigate the behavior and distribution of the technetium-labelled lipoproteins in vivo.

Two New Zealand White rabbits (2–3 kg) were injected intravenously with $^{99}$Tc-LDL (0.15 uCi, 1.7 mg human LDL protein) prepared according to my methods and filtered through a 0.22 micron filter just prior to injection. Blood samples were collected at intervals over a 36 hour period post-injection. After each collection, plasma was separated at 4° C. and divided into aliquots for radioactivity measurements and for isolation of $^{99}$Tc-LDL by ultracentrifugation at a density of 1.063 g/ml.

Plasma clearance of human $^{99}$Tc-LDL from the rabbit was biexponential, the slower component had a half-life of 18–22 hours, similar to previous results obtained with $^{125}$I-LDL. Blood samples that were drawn from 1 to 12 hours post injection and ultracentrifuged demonstrated 70–80% of the plasma radioactivity in the floating fraction which contained the LDL.

Similarly, 16 other rabbits were injected intravenously with $^{99m}$Tc-LDL, (4–8 mCi, 1.5 mg protein). Sixteeen hours after injection, the rabbits were anesthetized and imaged anteriorly and posteriorly with a standard Anger scintillation camera (Technicare 550) with a parallel hole collimator. Imaging time was 10 minutes and approximately 300,000 counts were obtained during this time. In all of the animals, accumulation of radioactivity by the adrenals, liver, kidneys, spleen and intestine was evident. Eighteen hours post injection, the rabbits were sacrificed and the organs were removed, cleaned, weighed and the radioactivity was counted. The biodistribution of $^{99m}$Tc-LDL is expressed in percent of injected radioactivity per gram and per organ, as shown in Table 1.

TABLE 1

Biodistribution of $^{99m}$Tc-LDL in the Rabbit

| Organ | Percent of Injected Radioactivity per Gram (mean ± S.E.M.) | Percent of Injected Radioactivity per organ (mean ± S.E.M.) |
|---|---|---|
| Venous Blood | 0.03 ± 0.01 | — |
| Liver | 0.19 ± 0.02 | 21.1 ± 1.3 |
| Spleen | 0.22 ± 0.04 | 0.4 ± 0.1 |
| Adrenal (whole)* | 0.81 ± 0.19 | 0.2 ± 0.1 |
| (cortex)* | 0.92 ± 0.09 | 0.3 ± 0.1 |
| (medulla)* | 0.59 ± 0.06 | 0.1 ± 0.1 |
| Kidney (cortex) | 0.11 ± 0.02 | 2.9 ± 0.4 |
| (medulla) | 0.04 ± 0.01 | 0.9 ± 0.2 |
| Small Bowel | 0.01 ± 0.00 | 1.3 ± 0.2** |
| Large Bowel | 0.05 ± 0.01 | 2.3 ± 0.3** |
| Muscle | 0.002 ± 0.0 | 1.6 ± 0.3** |
| Aorta (thoracic) | 0.02 ± 0.00 | — |

*The entire adrenal gland was weighed and counted in 12 animals, while cortex and medulla were dissected out, weighed, and counted separately in 4 animals.
**Percent of the injected dose is expressed per 100 gm for small and large bowel, while that for muscle is expressed for body muscle mass, assumed to be 45% of body weight.

The intersity of the image visualized for each organ was found to be proportional to the radioactivity measured in the biodistribution study.

It can be seen from the foregoing description that technetium labelled lipoproteins can be prepared easily by simultaneous reduction of pertechnetate and LDL with sodium dithionite at pH 9. Furthermore, low density lipoproteins labelled by this method substantially retain their native structure and biological function. They are thus suitable as probes for extracorporeal imaging to analyze lipoprotein metabolism.

It will thus be seen that the objects set forth above, among those made apparent from the preceeding description are efficiently attained. Also, certain changes may be made in carrying out the above constructions without departing from the scope of the invention.

For example, instead of using technetium, it is possible to use other isotopes suitable for imaging, such as indium, lead or mercury, by chelating to DTPA-LDL. Also, for some lipoprotein metabolism studies, chemically altered lipoprotein molecules may be used, or an active amino acid sequence of the molecule. For example, LDL is known to bind to certain organs through a high affinity receptor, which involves the lysine and arginine residues of LDL. However, patients who have a congenital deficiency in, or total lack of, this high-affinity receptor are known to have early and severe atherosclerosis, with high concentrations of LDL in their arteries. Thus, the mechanism of arterial LDL accumulation must be mediated through a different receptor from the high-affinity LDL receptor and a different receptor-binding portion of the LDL molecule. Reductive methylation of LDL has been shown to abolish this high affinity-receptor binding of LDL. Accordingly, methylated Tc-LDL should be desirable for use as a probe for extracorporeal imaging of arteries because it still binds to arterial lesions while having a reduced affinity for binding sites in other organs. Thus it is believed that it will provide an arterial image with less uptake by other organs and thus less confusing background radioactivity.

It is also believed that synthesis of an oligopeptide containing an amino acid sequence which binds to the arterial wall, and labelling this peptide with technetium would produce a stable, totally synthetic imaging agent for detecting arterial injury and atherosclerosis.

Accordingly, it is intended that the matter contained in the above description and shown in the accompanying figures be interpreted as illustrative and not in a limiting sense.

It is also to be understood that the following claims are intended to cover all the generic and specific features of the invention herein described.

What is claimed as new and desired to be secured by the Letters Patent of the United States is:

1. A method for radiolabelling a low density lipoprotein with an isotope of technetium, said isotope selected from the gorup consisting of technetium-99 and technetium-99m, said method comprising:
   A. mixing said lipoprotein and technetium isotope with sodium dithionite at a pH environment between 8 and 9 to form a stable technetium-lipoprotein complex, and
   B. separating the technetium-lipoprotein complex from the material resulting from step A.

2. A method for radiolabelling a low density lipoprotein according to claim 1 wherein the molar ratio of reducing agent to technetium isotope is greater than $10^6$.

3. A method for radiolabelling a lipoprotein with an isotope of technetium according to claim 1 wherein the lipoprotein consists essentially of lipoproteins having a density of 1.025 to 1.050 g/ml.

4. A method for radiolabelling a lipoprotein with an isotope of technetium according to claim 1 wherein the technetium-lipoprotein complex is separated from the material resulting from step A by molecular sieve chromatography.

5. A method for radiolabelling a lipoprotein with an isotope of technetium according to claim 1 wherein the technetium-lipoprotein complex is separated from the material resulting from step A by filtration and washing through a controlled pore size filter that substantially retains the technetium-lipoprotein complex.

6. A method for radiolabelling a low density lipoprotein with a technetium isotope, said isotope selected from the group consisting of technetium-99 and technetium-99m, said method comprising mixing the lipoprotein and the technetium isotope with sodium dithionite at a pH environment between 8 and 9 to form a stable technetium-lipoprotein complex.

7. A radiolabelled probe prepared by

A. exposing a low density lipoprotein and a technetium isotope, said isotope selected from the group consisting of technetium-99 and technetium-99m, to sodium dithionite at a pH environment between 8 and 9, to form a stable technetium-lipoprotein complex, and B. separating the technetium-lipoprotein complex from the material resulting from step A.

8. A radiolabelled probe prepared by exposing a low density lipoprotein and a technetium isotope, said isotope being selected from the group consisting of technetium 99m and technetium 99, with sodium dithionite at a pH environment between 8 and 9 to form a stable technetium-lipoprotein complex.

9. A technetium-99m-radiolabelled low density lipoprotein in a solution of sodium dithionite in a pH environment between 8 and 9.

10. A probe for detecting accumulation of low density lipoproteins in an arterial wall, said probe comprising a technetium-99m-labelled low density lipoprotein in a solution having a pH between 8 and 9.

11. A method for detecting accumulation of low density lipoproteins in an arterial wall, said method comprising the steps of A. preparing a technetium-99m-labelled low density lipoprotein in a solution having a pH between 8 and 9;

B. injecting said labelled low density lipoprotein into the vascular system of a patient;

C. subsequently viewing the patient's vascular system with extracorporeally-located detecting means capable of detecting the labelled low density lipoprotein;

D. determining from said detecting means the locations of the labelled low density lipoproteins; and E. quantifying concentrations of the labelled low density lipoproteins at the locations to determine the acumulation of said lipoproteins.

* * * * *